US 6,706,069 B2

(12) United States Patent
Berger

(10) Patent No.: US 6,706,069 B2
(45) Date of Patent: Mar. 16, 2004

(54) SPINAL GROOVED DIRECTOR WITH BUILT IN BALLOON

(76) Inventor: J. Lee Berger, 895 Mohawk Rd., Franklin Lakes, NJ (US) 07417

( * ) Notice: Subject to any disclaimer, the term of this patent is extended or adjusted under 35 U.S.C. 154(b) by 119 days.

(21) Appl. No.: 09/950,581

(22) Filed: Sep. 13, 2001

(65) Prior Publication Data

US 2003/0050702 A1 Mar. 13, 2003

(51) Int. Cl.$^7$ ................................................. A61F 2/44
(52) U.S. Cl. ................................................. 623/17.12
(58) Field of Search ........................ 604/97.01–97.03, 604/103.07, 916, 96.01, 101.01; 606/86, 92–94, 105, 191, 192; 600/29–31

(56) References Cited

U.S. PATENT DOCUMENTS

| | | | |
|---|---|---|---|
| 4,217,903 A | * | 8/1980 | Witherow .............. 604/102.03 |
| 4,313,434 A | | 2/1982 | Segal |
| 4,969,888 A | | 11/1990 | Scholten et al. |
| 5,108,404 A | | 4/1992 | Scholten et al. |
| 5,423,850 A | | 6/1995 | Berger |
| 5,449,344 A | * | 9/1995 | Taylor et al. ............ 604/97.03 |
| 5,480,400 A | | 1/1996 | Berger |
| 5,972,015 A | | 10/1999 | Scribner et al. |
| 6,167,886 B1 | * | 1/2001 | Engel et al. ................. 128/885 |
| 6,241,734 B1 | | 6/2001 | Scribner et al. |
| 6,248,110 B1 | | 6/2001 | Reiley et al. |
| 6,558,350 B1 | * | 5/2003 | Hart et al. ................... 604/104 |

* cited by examiner

Primary Examiner—Kevin Shaver
Assistant Examiner—Michael B. Priddy
(74) Attorney, Agent, or Firm—John S. Hale; Gipple & Hale

(57) ABSTRACT

The present invention is directed toward a grooved director with a built in balloon which is inflated by a pump to a predetermined pressure to expand the walls of a collapsed vertebra. The device is inserted into the body of the compressed vertebra and the grooved director is positioned and aimed in a direction under the compressed superior end plate of the vertebral body. The balloon inside of the grooved director is inflated and the force and direction of balloon inflation restores the height of the fractured vertebrae. The balloon is deflated and the grooved director is circumferentially rotated while intermittently inflating and deflating the balloon to creates a symmetrical space within the center of the vertebral body. The balloon is deflated and the grooved director device with balloon is removed leaving a rebuilt vertebra which may be filled with a biocompatible material.

16 Claims, 4 Drawing Sheets

SPINAL GROOVED DIRECTOR WITH BUILT IN BALLOON

FIELD OF THE INVENTION

The invention relates to expandable structures, which in use, are deployed in interior body regions of humans and other animals. More particularly, the present invention is directed to an apparatus and method for extending a balloon in an crushed vertebra by sequentially inflating a balloon in a groove director and filling the open chamber of the vertebrae with osteogenic material.

BACKGROUND OF THE INVENTION

When cancellous bone becomes diseased for various reasons such as a result of osteoporosis, avascular necrosis, cancer or other diseases, the surrounding cortical bone becomes prone to compression fracture or collapse because the cancerous bone does not provide the necessary interior support for the surrounding cortical bone. The treatment of such collapsed or fractured bone has utilized a number of medical devices.

One type of medical devices used in the treatment of collapsed or fractured bone utilizes expandable structures to reconstitute the structure of the bone. The deployment of expandable structures into interior body regions for various medical purposes is well known in the medical art. For example, expandable structures, generically called "balloons," are deployed during angioplasty to open occluded blood vessels. As another example, U.S. Pat. Nos. 4,969,888 and 5,108,404 disclose apparatus and methods the use of expandable structures for the fixation of fractures or other osteoporotic and non-osteoporotic conditions of human and animal bones.

U.S. Pat. No. 4,313,434 to Segal describes a method for fixation of fracture of long bones using a flexible, inflatable bladder inside the intramedullar cavity. A small opening is drilled in the bone, and the bladder is inserted through the hole into the intramedullar cavity. The bladder is then inflated with sterile air and sealed, to fixate the bone. After the fracture has healed, the bladder is deflated and removed.

U.S. Pat. Nos. 5,423,850 and 5,480,400 both to Berger, the inventor of the present application, describe methods and devices of bone fixation using a balloon catheter. The catheter, with the deflated balloon at its distal end, is inserted into the intramedullar cavity, past the fracture site. In the '850 patent, the balloon is inserted by guiding it along guide wires that are fed through the cavity, before introducing the catheter. Once fully inserted in the cavity, the balloon is inflated to anchor it in place, and the catheter is tightened against the balloon to provide compression to the fracture.

These patents provide only a joining effect as in the pulling of one broken bone towards the other.

Various medical apparatus currently used, include balloon expandable devices where an expandable balloon is used to change the shape of an implant or a collapsed or fracture vertebrae. Such balloon devices use hydraulic pressure by the insertion of fluid into the balloon's interior, thereby enlarging the balloon's diameter. The pressure of the fluid within the sealed balloon provides the energy to support the balloon in its expanded shape. These types of vertebral balloons inflate spherically in all directions and it is difficult to guide and control the force of expansion in the vertebrae resulting in uneven application of force with portions of a crushed vertebra not being expanded to the original configuration.

U.S. Pat. No. 5,972,015 is directed toward a device intended for deployment into interior body regions employing a catheter tube which carries an expandable structure. The structure can include spaced apart end regions which provide a non-conical diameter transition between the diameter of the catheter tube and the larger diameter of the expanded structure. The non-conical diameter transition mitigates the tradeoff, present in other balloon structures between achieving a desired maximum expanded diameter without undesired reduction in the effective length of the structure.

U.S. Pat. No. 6,241,734 discloses a system and method for delivering material into a bone deploying a cannula through soft tissue to establish a subcutaneous path into the bone. A material is introduced into the bone through the cannula. The apparatus and method advance a tamping instrument having a body including markings located along the length in increments from the terminus which allow the physician to gauge the position of the instrument in the subcutaneous path as material is being tamped into the bone. The tamping instrument is deployed through the cannula to urge material residing in the cannula into the bone and deliver a material at a pressure which is no greater no greater than about 360 psi.

U.S. Pat. No. 6,248,110 is a system and method for treating fractured or diseased bone by deploying several therapeutic tools into the bone. An expandable balloon body is deployed in association with a bone cement nozzle into the bone such that both occupy the bone interior at the same time. Expansion of the balloon body forms cavities in the cancerous bone in the interior bone volume.

It is important to maximize the size and surface area of an expandable structure when deployed in an interior body region. Current medical balloons manufactured by molding techniques are designed to be guided into a narrow channel, such as a blood vessel or the fallopian tube, where they are then inflated. In this environment, the diameter of the balloon is critical to its success, but the length is less so. Such balloons only need to be long enough to cross the area of intended use, with few constraints past the effective portion of the inflated balloon. This allows conventional balloons to be constructed in three molded pieces, comprising a cylindrical middle section and two conical ends, bonded to a catheter shaft. As a practical matter, neither the length of the conical end, nor the length of the bond of the balloon to the catheter shaft, affect the function of conventional balloons, and these regions on conventional balloons are often 1 cm in length or more. Indeed, the larger the balloon diameter, the longer the end cone, which creates a tradeoff between maximum effective length and maximum effective diameter. This tradeoff makes optimization of conventional structures problematic in interior structures with defined lengths, such as bone.

Vertebroplasty is a recent surgical technique which uses the injection of a cement material into a collapsing vertebral body. Osteoporosis is the leading cause of vertebral fracture. Approximately 700,00 vertebral fractures occur annually in the United States. The procedure is performed to reinforce the fractured bone, alleviate chronic back and prevent further vertebral collapse. Vertebroplasty was developed in France in the 1980's but is relatively new in the United States and is presently available in only a few hospitals.

Deramond et al., "Percutaneous vertebroplasty with methyl-methacrylate: technique, method, results [abstract]." Radiology 1990;117 (suppl):352; among others, have described the percutaneous injection of PMMA into vertebral compression fractures by the transpedicular or paravertebral approach under CT and/or fluoroscopic guidance. Percutaneous vertebroplasty is desirable from the standpoint that it is minimally invasive, compared to the alternative of surgically exposing the hard tissue site to be supplemented with PMMA or other filler.

The general procedure for performing percutaneous vertebroplasty includes the percutaneous injection of PMMA or other bone implant material into the damaged or fractured bone tissue of a vertebra. During injection of the bone implant material, fluoroscopic imaging or another imaging technique is used to track the path that the bone implant material takes as well as its final position upon implantation. Contrast agents such as barium sulfate powder are often used to aid the visibility of the bone implant material by imaging. This type of contrast agent is fairly effective once a given mass of the mixture of it with the bone implant material has accumulated at an implant site. However, for purposes of tracking the flow and leading edge surfaces of a bone implant material during injection, or for viewing small volumes of the implant material, the contrast agents presently used are adequate.

As an adjunct to the balloon devices, a material which solidifies (e.g. by polymerization) is inserted into a balloon, forming a solid which has a new shape. This material can have two-component cement properties, and can be formed of epoxy or polymer. The material is compressed into the balloon and solidifies by change in temperature or humidity.

SUMMARY OF THE INVENTION

One aspect of the invention provides a device for deployment into an interior body region comprising a grooved director tube, which carries an expandable structure. The structure preferably a balloon is adapted to assume a collapsed geometry for deployment into the vertebra and an expanded geometry for use within the vertebra. The grooved director extends along a first axis and the geometry of the balloon extends outward from that axis against the vertebra walls restoring the same to their original configuration. This permits sequential deployment of the balloon in a symmetric fashion with respect to the natural axis of a targeted interior body region, even when the groove director is not aligned with the natural axis.

After the vertebra walls have been expanded by the balloon, a slurry or paste of biocompatible filler material is placed inside the vertebra. The hard tissue implant material may be mixed with the radiopaque particles and include hydroxy apatite, various formulations of biocompatible calcium phosphates, biocompatible calcium sulfates, demineralized and/or mineralized bone particles, polymer based implants including polyglycolic acid and/or polylactic acid compounds, collagen and/or collagen derivative preparations alone or in combination with other biomaterials, chitin and/or chitosan preparations, bioglasses including oxides of silicon, sodium, calcium and phosphorous and combinations thereof, and other known materials which are acceptable for use as hard tissue implant materials including osteogenic and osteoinductive compositions, and combinations thereof.

It is an object of the present invention to provide a device which is able to guide, concentrate, control and improve the force of balloon compression in a collapsed vertebral body.

It is another object of the invention to provide a device which can be rotated in the vertebral body to provide selected areas of force against cancerous bone and cortical bone of the vertebral body.

It is yet another object of the invention to provide a device to deliver bone graft material or cement into a vertebral body after expansion of same.

In the accompanying drawings, there is shown an illustrative embodiment of the invention from which these and other objectives, novel features and advantages will be readily apparent.

DETAILED DESCRIPTION OF THE PREFERRED EMBODIMENT

Figure 1:
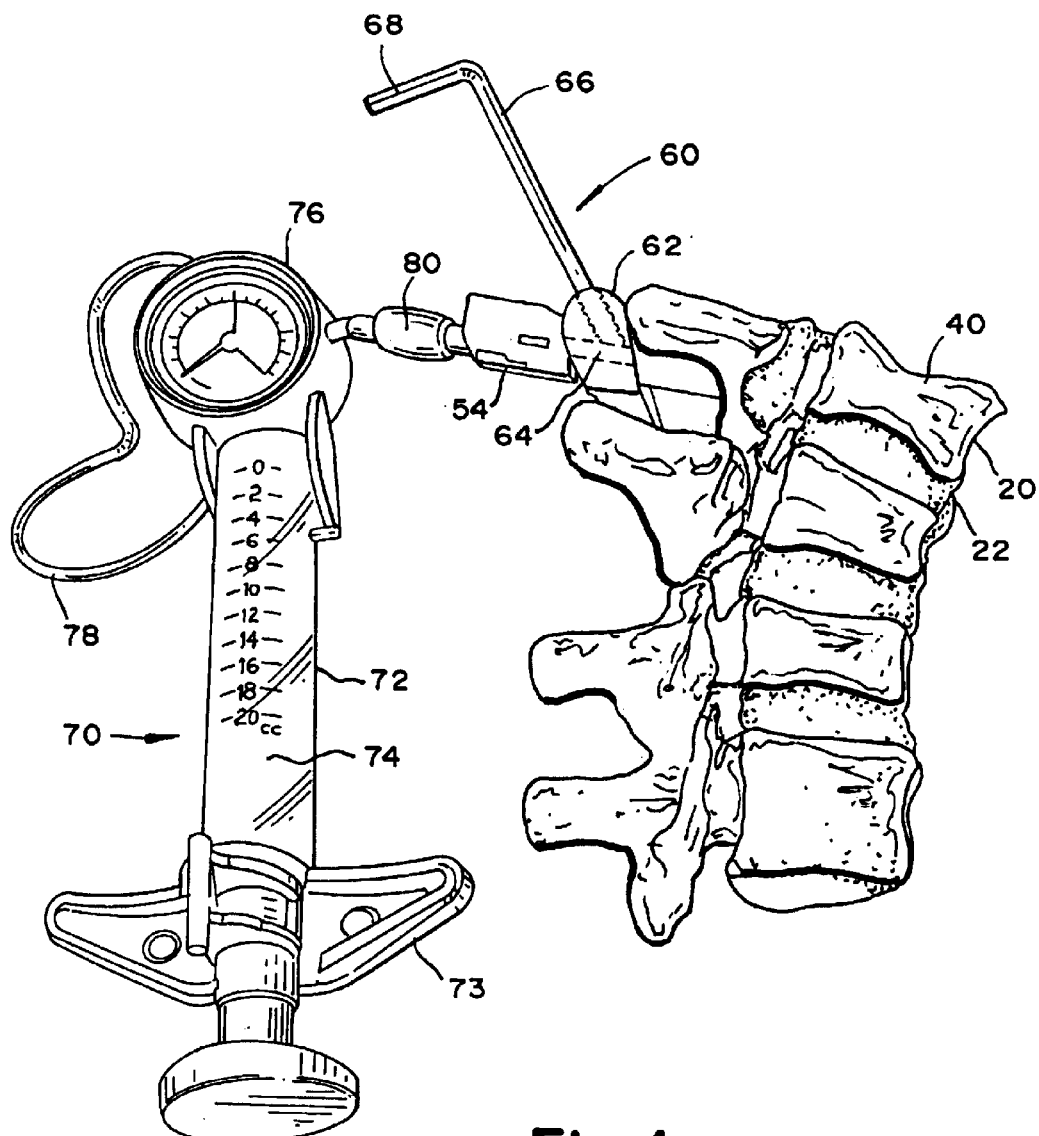
FIG. 1 is a perspective view of the inventive apparatus inserted into a sectional view of the damaged vertebra.
Figure 2:
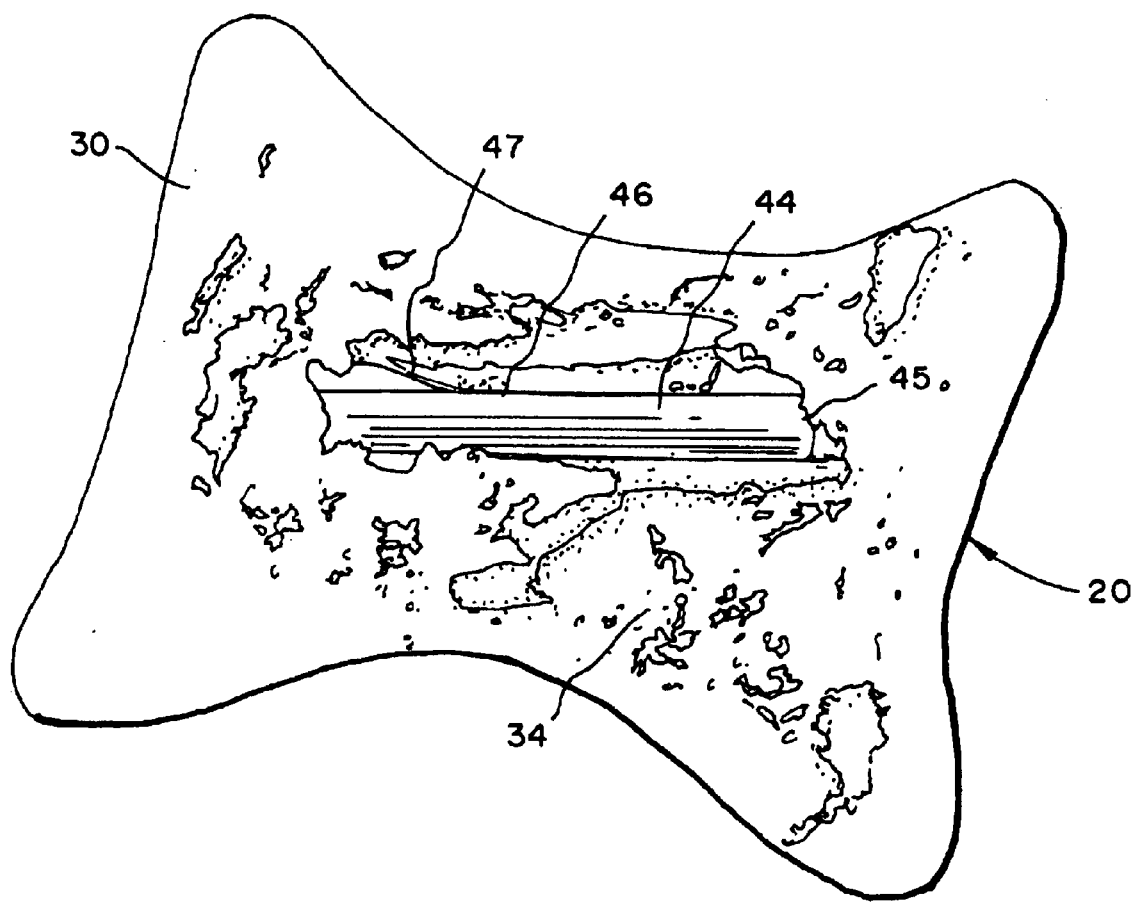
FIG. 2 is an enlarged perspective view of the grooved director in a vertebral body prior to expansion of the balloon.
Figure 3:
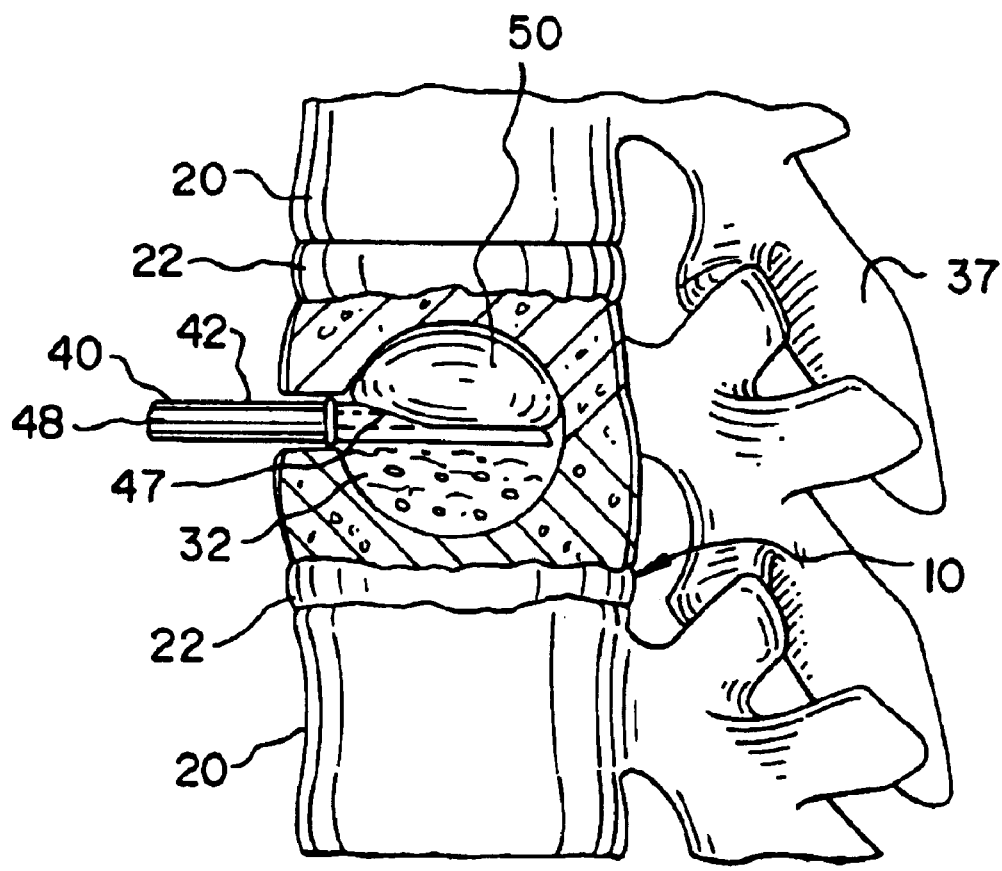
FIG. 3 is a sectional view of an injection of the grooved director into the interior volume of the vertebra and the balloon expanded against a wall of the damaged vertebra.
Figure 4:
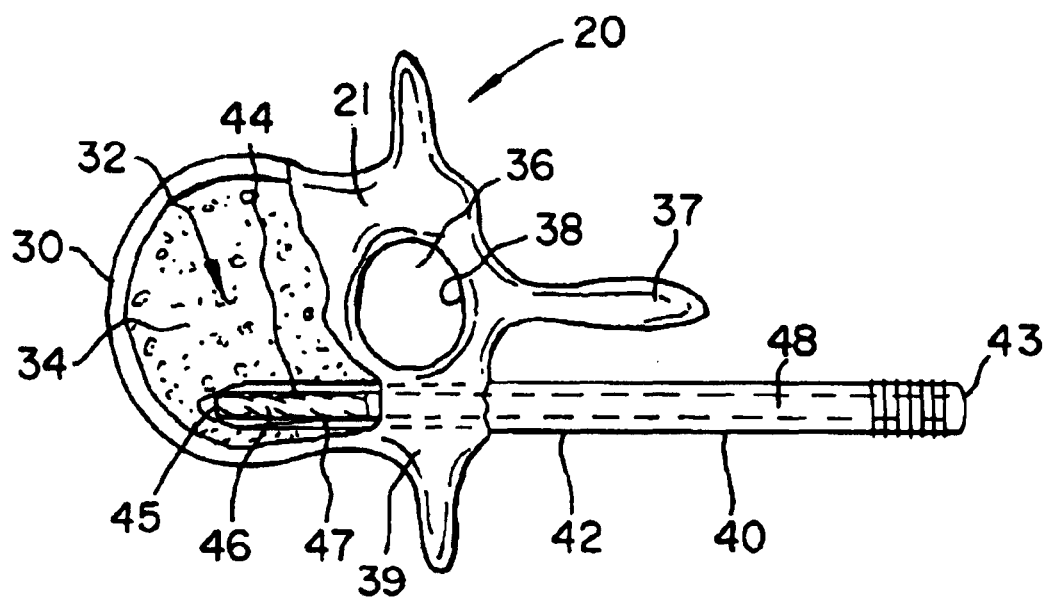
FIG. 4 is a cross sectional view of a restored vertebra filled with implant material with the grooved director still inserted in the vertebra.

The best mode and the preferred embodiment of the inventive grooved director and balloon apparatus is shown generally in FIGS. 1–4.

The invention is primarily directed toward the treatment of vertebrae of the spine 10. The geometry of the vertebral body 20 generally includes an exterior formed from compact cortical bone 30 and an interior volume 32 of reticulated cancellous, or spongy, bone 34 (also called medullary bone or trabecular bone). The vertebrae are separated from each other by discs 22.

The spinal canal 36 (see FIG. 4), is located on the posterior (i.e., back) side of each vertebra 20. The spinal cord (not shown) passes through the spinal canal 36. The vertebral arch 38 surrounds the spinal canal 36. The spinous process 37 extends from the rear of the vertebral arch 38. Left and right pedicles 39 of the vertebral arch 38 adjoin the vertebral body 21.

The grooved director 40 can be inserted into bone in accordance with the teachings of the above described U.S. Pat. Nos. 4,969,888 and 5,108,404 which are incorporated herein by reference. For a vertebral body 21, access into the interior volume 32 can be accomplished, for example, by drilling an access portal through either pedicle. This is called a transpedicular approach and the access portal aligns the axis of the grooved director tube 40 obliquely with respect to all natural axes of the vertebral body 21.

The grooved director 40 is constructed of a single piece of stainless steel or plastic tube 42 with a distal threaded end 43 which can be screwed into connector member 54 and a proximal cutout end 44 having a blunt rounded edged tip 45. The cutout end 44 defines a groove 46 which forms the seat for the balloon. The groove 46 runs along the upper surface of the end 44 and leads to a lumen 48 which is formed by and extends through the tube 42. The intersection of the groove 46 and lumen 48 is marked by a beveled cut away section 47.

A balloon 50 is moveably mounted within the lumen 48 of the groove director for expansion within the interior volume 32 of the vertebra 20 away from the axis of the grooved director 50 compressing cancerous bone 34 and pushing the cortical walls outward to form an internal cavity approximating the original shape. The material of the balloon 50 can be selected according to the therapeutic objectives of its use. For example, materials including vinyl, nylon, polyethylenes, ionomer, polyurethane, and polyethylenetetraphthalate (PET) can be used. The thickness of the structure is typically in the range of 1 micron to 20 microns of thicknesses that can withstand pressures of up to 250–750 psi. The thickness of the structure is typically in the range of 1 micron to 20 microns of thicknesses that can withstand pressures of up to 250–750 psi.

If desired, the material for the balloon structure can be selected to exhibit elastic properties, like latex or less elastic properties, like silicone. Using expandable bodies with generally elastic or generally semi-elastic properties, the physician monitors the expansion to assure that over-expansion and wall failure do not occur.

The asymmetric compaction of cancerous bone 34 in the interior volume 32 may also exert unequal or nonuniform interior forces upon cortical bone 30, making it difficult to elevate or push broken and compressed bone. The grooved director is rotated 90° or a lesser or greater amount and the process is repeated until the walls of the vertebrae are reestablished to its essentially original form.

The grooved director is kept in a fixed position with respect to the vertebrae being operated on by locking mechanism 60 which can be attached via a frame to the operating table. When the balloon is inflated the anti-torque locating mechanism will inhibit downward displacement of the grooved director and protect the pedicle. The locking mechanism is constructed with a housing 62 provided with a through going bore 64 into which the tubular shaped grooved director member 40 is inserted until the connector housing 54 located on the distal end of the grooved director member 40 abuts the locking mechanism housing 62. A partially threaded bore 65 (not shown) is cut into the housing 62 transverse to and intersecting the through going bore 64. A locking handle member 66 with a threaded distal end 67 (not shown) is mounted in the partially threaded bore 65 and upon rotation by a handle portion 68 engages the tubular body of the grooved director holding the same in a locked position within the locking mechanism housing 62 so that the same cannot move. This allows direction of the balloon away from its seat on the upper surface of end 44 and groove 46 of the grooved director 40 in a predetermined selected direction toward a particular segment of the vertebrae wall. A pump assembly 70 is connected to the distal end of the tubular groove body to supply fluid to the balloon to inflate the balloon inside the vertebrae. The pump assembly 70 is constructed with a syringe body 72 having a handle 73 with a plunger 74 mounted therein, a pressure gauge 76 mounted at the distal end of the syringe body, flexible tubing 78 leading from the distal tip of the syringe body and a connector tip 80 located on the distal end of the flexible tubing which can be snap fit by a bayonet or screw thread means into the connector member 54. The plunger 74 can be a standard straight cylindrical wall type or can have external threads which provide a screw in pressure on the fluid container in the body of the syringe. Thus the surgeon is able to determine the pressure being applied to the inside of the vertebrae by viewing the reading on the gauge 76.

In operation, the grooved director with the built-in balloon is inserted into the body of the compressed vertebra through a pedicular or extrapedicular approach. Preferably, after the balloon is inserted into the bone, the balloon is filled with non-compressible fluid. In the preferred embodiments, the balloon has a valve to prevent fluid from escaping (while also allowing fluid to be released, once desired). Upon filing the balloon with fluid, it expands so that it substantially fills the portion of the intramedullar cavity which is to be expanded. Preferably, an X-ray or fluoroscopy or other imaging technique is taken of the bone with the balloon inside (preferably while the balloon is stir in a partially or non-expanded state). The balloon's internal structure is then observed in the image to ascertain that the balloon is properly positioned, before fully inflating the balloon with the hydraulic fluid. In particular, the grooved director will show up on the image so that proper positioning can be verified. The grooved director 40 is positioned and aimed in a direction under the compressed superior end plate of the vertebral body. The balloon 50 inside of the grooved director is extended and inflated or if it is fixed to lie on the face 44 it is inflated so that the force and direction of balloon inflation reduces and restores the height of the fractured vertebra. The balloon is deflated and the grooved director is circumferentially rotated intermittently inflating the balloon at the same pressure or varying pressures if such is deemed necessary. This creates a symmetrical space within the center of the vertebral body. The balloon is deflated and the grooved director device with balloon is removed from the trochar insertion sheath. A grooved director without balloon is then inserted through the trochar insertion sheath into the space within the center of the vertebral body.

A syringe filled with bone graft substitute pellets of demineralized bone pellets such as those manufactured by Musculoskeletal Transplant Foundation, Osteotech Inc. or non allograft bone graft substitute material such as the material OSTEOSET, a surgical grade calcium sulfate manufactured by Wright Medical Inc. are inserted through the grooved director and packed into the space within the center of the vertebral body followed by an injection of ALLOMATRIX putty manufactured by Wright Medical, Inc., DBX putty or gel, Manufactured by Musculoskeletal Transplant Foundation or GRAFTON putty or gel manufactured by Osteotech Inc. to seal the graft in place. A trochar insertion sheath which has previously been inserted in the initial drilled opening is removed and a cap or bone cement is used to fill the insertion entrance.

In addition to the materials listed above, hard tissue implant materials that may be used include hydroxyapatite, various formulations of biocompatible calcium phosphates, biocompatible calcium sulfates, demineralized and/or mineralized bone particles, polymer based implants including polyglycolic acid and/or polylactic acid compounds, collagen and/or collagen derivative preparations alone or in combination with other biomaterials, chitin and/or chitosan preparations, bioglasses including oxides of silicon, sodium, calcium and phosphorous and combinations thereof.

If desired a percutaneous injection of polymethyl methacrylate (PMMA) in a slurry state can be percutaneously injected. The slurry is prepared just prior to the injection by mixing a powder component, e.g., methyl methacrylate polymer, with a liquid component, e.g., methylmethacrylate monomer. Additional components such as copolymers (e.g., styrene,), accelerators (e.g., N,N-imethyl paratoluidene), initiators (e.g., benzoyl peroxide), stabilizers (e.g., hydroquinone) and/or antibiotics (e.g., Tobramycin) may be included in the slurry. The above are only examples of the many additives that are currently used in for implantation, and the other known additives are acceptable for the purposes of the present invention.

In another embodiment of the present invention, the balloon fixture is also preferably inserted using a grooved director. After the placement of the grooved director in the intramedullary space, a sleeve can be inserted therein, through which the balloon is inserted. The balloon is positioned and inflated to fixated with a biocompatible solidifying fluid under pressure from an external source, causing the balloon to expand radially outward to expand and fixate the walls of the vertebra. The grooved director is removed, the balloon is then sealed, and the external fluid source is disconnected and detached from the inflating device leaving the implanted filled balloon.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. A grooved director apparatus to aid in the insertion of a balloon catheter into a vertebra comprising an elongated substantially rigid tubular member defining a longitudinal axis with an internal bore and a closed distal end, an inflatable balloon moveably mounted in said tubular member, said tubular member being cut away from a point along the longitudinal axis to said closed distal tip forming a balloon seat adjacent said internal bore allowing directed expansion of said balloon away from said longitudinal axis seat toward an area to which compression is to be applied allowing guidance and control of the force of expansion in the vertebra, anchor means mounted to said tubular member keeping said tubular member in a fixed position when said balloon is inflated while allowing selective circumferential rotation of said tubular member to a new position within said vertebra when said balloon is deflated to reposition said balloon within said vertebra and pump means fluidly connected to said rigid tubular member to apply selected fluid pressure to said balloon, said pump means including a pressure gauge connected thereto and a connector conduit means communicating with said internal bore to provide fluid communication with said balloon to inflate and deflate said balloon.

2. A grooved director apparatus as claimed in claim 1 wherein said balloon includes a guide wire.

3. A grooved director apparatus as claimed in claim 1 wherein said connector conduit comprises a flexible tubing mounted to said tip of said syringe to transport flowable material from said syringe and a locking tip mounted to a distal end of said flexible tubing, said locking tip being adapted to be locked in a fixed position relative to said rigid groove director.

4. A grooved director apparatus to aid in the insertion of a balloon catheter into a vertebra comprising an elongated substantially rigid tubular member with a longitudinal axis defining an internal bore, a cut away seat portion adjacent said internal bore and a rounded solid closed distal end, an inflatable balloon mounted in said tubular member, said tubular member being cut away from a point along the longitudinal axis toward said closed distal end forming a balloon seat for said inflatable balloon, said seat allowing directed expansion of said balloon away from said longitudinal axis toward an area to which compression is to be applied allowing guidance of balloon expansion and control of the force of expansion in the vertebra, anchor means mounted to said tubular member keeping said tubular member in a fixed position when said balloon is inflated while allowing for selective rotation of said tubular member when said balloon is deflated and pump means fluidly connected to said rigid tubular member to apply selected fluid pressure to said balloon.

5. A grooved director apparatus as claimed in claim 4 wherein said tubular member is stainless steel.

6. A grooved director apparatus as claimed in claim 4 wherein said pump means comprises a syringe body, a plunger mounted in said syringe body, a pressure gauge mounted at the distal end of said syringe body and a connector conduit leading from a tip at the end of said syringe body to allow fluid communication with said balloon.

7. A grooved director apparatus as claimed in claim 6 wherein said syringe body has a cylindrical housing and said plunger has a cylindrical body, said syringe body being provided with locking means to lock said plunger in a fixed position within said body.

8. A grooved director apparatus as claimed in claim 6 wherein said syringe body has a cylindrical housing with internal threading, and said plunger has a cylindrical body with external threading.

9. A grooved director apparatus as claimed in claim 6 wherein said syringe body includes a handle mechanism comprising a syringe housing with at least two wing members extending outward from the syringe housing to provide easy grasping of the syringe housing.

10. A grooved director apparatus to aid in the insertion of a balloon catheter into a vertebra comprising an elongated substantially rigid tubular member defining a longitudinal axis with a closed distal tip and an open proximal end portion, an inflatable balloon mounted in said tubular member, said tubular member being cut away from a point along the longitudinal axis to said closed distal tip forming a balloon seat allowing directed expansion of said balloon away from said longitudinal axis toward an area to which compression is to be applied allowing guidance and control of the force of expansion in the vertebra, anchor means mounted to said tubular member keeping said tubular member in a fixed position when said balloon is inflated while allowing selective circumferential rotation of said tubular member when said balloon is deflated and pump means fluidly connected to said rigid tubular member to apply selected fluid pressure to said balloon, said anchor means comprises a housing defining a through going bore for receiving said rigid tubular member, a second bore intersecting said through going bore and a locking member mounted in said second bore adapted to engage said rigid tubular member and hold the same in a locked position.

11. A grooved director apparatus to aid in the insertion of a balloon catheter into a vertebra comprising an elongated substantially rigid tubular member defining a longitudinal axis with a closed distal tip and an open proximal end portion, an inflatable balloon mounted in said tubular member, said tubular member being cut away from a point along the longitudinal axis to said closed distal tip forming a balloon seat allowing directed expansion of said balloon away from said longitudinal axis toward an area to which compression is to be applied allowing guidance and control of the force of expansion in the vertebra, anchor means mounted to said tubular member keeping said tubular member in a fixed position when said balloon is inflated while allowing selective circumferential rotation of said tubular member when said balloon is deflated and pump means fluidly connected to said rigid tubular member to apply selected fluid pressure to said balloon, said pump means including a flexible tubing connected to the distal end of a syringe to transport flowable material from said syringe and a bayonet type locking tip secured to the distal end of said flexible tubing, said locking tip being adapted to be locked in a fixed position relative to said rigid groove director.

12. A grooved director apparatus as claimed in claim 1 wherein said locking tip comprises a tip member with external threads.

13. A grooved director apparatus to aid in the insertion of a balloon catheter into a vertebra comprising an elongated substantially rigid tubular member defining a longitudinal axis with a closed distal tip and an open proximal end portion, an inflatable balloon moveably mounted in said tubular member, said tubular member being cut away from a point along the longitudinal axis to said closed distal tip forming a balloon seat allowing directed expansion of said balloon away from said longitudinal axis toward an area to which compression is to be applied allowing guidance and control of the force of expansion in the vertebra, anchor means mounted to said tubular member keeping said tubular member in a fixed position when said balloon is inflated while allowing selective circumferential rotation of said tubular member when said balloon is deflated and pump means fluidly connected to said rigid tubular member to apply selected fluid pressure to said balloon, said pump means comprising a syringe body, a plunger mounted in said syringe body, a pressure gauge mounted at the distal end of said syringe body and a connector conduit leading from a tip at the end of said syringe body to provide fluid communication with said balloon, including a connector member mounted to a distal end of said grooved director and adapted to hold a locking tip of said connector conduit.

14. A grooved director apparatus to aid in the insertion of a balloon catheter into a vertebra comprising an elongated substantially rigid tubular member defining a longitudinal axis with a closed distal tip and an open proximal end portion, an inflatable balloon moveably mounted in said tubular member, said tubular member being cut away from a point along the longitudinal axis to said closed distal tip forming a balloon seat allowing directed expansion of said balloon away from said longitudinal axis toward an area to which compression is to be applied allowing guidance and control of the force of expansion in the vertebra, anchor means mounted to said tubular member keeping said tubular member in a fixed position when said balloon is inflated while allowing selective circumferential rotation of said tubular member when said balloon is deflated and pump means fluidly connected to said rigid tubular member to apply selected fluid pressure to said balloon, said pump means comprising a syringe body, a plunger mounted in said syringe body, a pressure gauge mounted at the distal end of said syringe body and a connector conduit leading from a tip at the end of said syringe body to provide fluid communication with said balloon, said anchor means comprises a housing defining a through going bore for receiving said rigid tubular member, a second bore intersecting said through going bore and a locking member mounted in said second bore adapted to engage said rigid tubular member and hold the same in a locked position.

15. A grooved director apparatus to aid in the insertion of a balloon catheter into a vertebra comprising an elongated substantially rigid tubular member with a longitudinal axis defining an internal bore, a cut away seat portion adjacent said internal bore and a rounded solid digital end piece, a closed distal tip and proximal end portion, an inflatable balloon mounted in said tubular member, said tubular member being cut away from a point along the longitudinal axis toward said closed distal tip forming a balloon seat for said inflatable balloon, said seat allowing directed expansion of said balloon away from said longitudinal axis toward an area to which compression is to be applied allowing guidance of balloon expansion and control of the force of expansion in the vertebra, anchor means mounted to said tubular member keeping said tubular member in a fixed position when said balloon is inflated while allowing selective circumferential rotation of said tubular member when said balloon is deflated and pump means fluidly connected to said rigid tubular member to apply selected fluid pressure to said balloon, said internal bore being dimensioned for the transportation of osteogenic material through said bore.

16. A grooved director apparatus as claimed in claim 15 wherein said osteogenic material consists of a group selected from hydroxyapatite, various formulations of biocompatible calcium phosphates, biocompatible calcium sulfates, demineralized and/or mineralized bone particles, collagen and/or collagen derivative preparations alone or in combination with other biomaterials, chitin and/or chitosan preparations.

* * * * *